(12) United States Patent
Pedersen et al.

(10) Patent No.: US 6,518,240 B1
(45) Date of Patent: Feb. 11, 2003

(54) COMPOSITION AND METHOD FOR PREPARING AMINO ACID CHELATES AND COMPLEXES

(75) Inventors: Mark Pedersen, Kaysville, UT (US); H. DeWayne Ashmead, Fruit Heights, UT (US)

(73) Assignee: Albion International, Inc., Clearfield, UT (US)

( * ) Notice: Subject to any disclaimer, the term of this patent is extended or adjusted under 35 U.S.C. 154(b) by 0 days.

(21) Appl. No.: 09/686,047

(22) Filed: Oct. 11, 2000

(51) Int. Cl.[7] .................. A61K 33/26; A61K 33/06; A61K 33/04; A61K 38/00; A61K 33/24; A61K 33/32; A01N 37/18; A01N 37/44; A01N 59/06

(52) U.S. Cl. .................................................. 514/2

(58) Field of Search ................... 424/295, 709, 424/617, 639, 646, 647, 648, 655, 682; 514/2, 561, 563

(56) References Cited

U.S. PATENT DOCUMENTS

| | | | |
|---|---|---|---|
| 2,877,253 A | | 3/1959 | Rummel |
| 2,957,806 A | | 10/1960 | Rummel |
| 2,960,406 A | | 11/1960 | Cardon |
| 3,396,104 A | | 8/1968 | Miller |
| 3,463,858 A | | 8/1969 | Anderson |
| 3,775,132 A | | 11/1973 | Richards, Jr. |
| 4,020,158 A | | 4/1977 | Ashmead |
| 4,067,994 A | * | 1/1978 | Anderson et al. ........... 424/295 |
| 4,103,003 A | | 7/1978 | Ashmead |
| 4,167,564 A | | 9/1979 | Jensen |
| 4,172,072 A | | 10/1979 | Ashmead |
| 4,183,947 A | * | 1/1980 | Cockerill .................... 424/295 |
| 4,216,143 A | | 8/1980 | Ashmead |
| 4,216,144 A | | 8/1980 | Ashmead |
| 4,599,152 A | | 7/1986 | Ashmead |
| 4,725,427 A | | 2/1988 | Ashmead et al. |
| 4,774,089 A | | 9/1988 | Ashmead |
| 4,830,716 A | | 5/1989 | Ashmead |
| 4,863,898 A | | 9/1989 | Ashmead et al. |

* cited by examiner

*Primary Examiner*—Alton N Pryor
(74) *Attorney, Agent, or Firm*—Thorpe North & Western, LLP

(57) ABSTRACT

Compositions and methods of preparing amino acid chelates and complexes are disclosed and described. Specifically, by (a) combining a hydrated metal sulfate salt with an amino acid ligand to form a particulate blend, (b) placing the particulate blend in an enclosed environment; and (c) applying heat to the particulate blend in the enclosed environment causing the waters of hydration of the metal sulfate salt to be released into the enclosed environment causing a reaction resulting in the formation of an amino acid chelate or complex by effecting the reaction between functional electron rich groups of the amino acid ligand and a metal ion of the metal sulfate salt. The waters of hydration serve to provide the water necessary to enable a bonding reaction to take place between the electron rich functional groups of the amino acid ligand and the metal ion of the hydrated metal sulfate salt.

10 Claims, No Drawings

COMPOSITION AND METHOD FOR PREPARING AMINO ACID CHELATES AND COMPLEXES

FIELD OF THE INVENTION

The present invention is drawn to compositions and methods of preparing amino acid chelates and complexes. Particularly, by combining a hydrated metal sulfate salt with an amino acid ligand as a particulate blend, placing the particulate blend in an enclosed environment, and applying heat to the particulate blend in the enclosed environment, the waters of hydration of the hydrated metal sulfate salt are caused to be released into the enclosed environment such that amino acid chelates and complexes are formed. The waters of hydration serve to provide the water necessary to enable a bonding reaction to take place between the electron rich functional groups of the amino acid ligand and the metal ion of the hydrated metal sulfate salt.

BACKGROUND OF THE INVENTION

A chelate is a definite structure resulting from precise requirements of synthesis. Proper conditions must be present for chelation to take place including proper mole ratios of ligands to metal ions, pH, and solubility of reactants. As such, traditional "wet" methods of preparing chelates have typically been used to prepare chelates. These methods include the step of dissolving raw materials in solution to ionize the solution or create an appropriate electronic configuration in order for bonding to develop. Though wet methods have typically been used to make chelates, chelates and/or complexes have also been made under dry conditions.

In U.S. Pat. Nos. 2,877,253 and 2,957,806, the entire teachings of which are incorporated by reference, a ferrous sulfate-glycine complex that is substantially free from ferric iron is disclosed. By following the process of dry blending and heating the reactants as is disclosed in these patents, at least some complexing and even some chelation occurs. In fact, the above patents teach that there is a distinct color change that takes place as a result of the reaction, i.e. the "complex turns uniformly light brown." However, the reactions described therein are not capable of reacting to completion. This is because a minimum amount of moisture is needed to drive the reaction. Because the reactions described in these patents are carried out in open air conditions, when the waters of hydration are liberated, the liberated water is exposed to the open atmosphere. Thus, some of the liberated water drives the reaction and some is evaporated.

The processes described in U.S. Pat. Nos. 2,877,253 and 2,957,806 have been recently improved as described in a copending U.S. patent application Ser. No. 09/686,683 filed of even date herewith entitled "A COMPOSITION AND METHOD FOR PREPARING AMINO ACID CHELATES AND COMPLEXES FREE OF INTERFERING COMPLEX IONS," the entire teachings of which are incorporated herein by reference. In that application, the reactions described therein are carried further than the reactions of the above referenced patents (or in many cases carried to completion) because all of the reactants are retained in an enclosed environment. Specifically, by minimizing or eliminating the evaporation of water released by the hydrated sulfate salt in the reaction blend, and by adding calcium oxide or calcium hydroxide in appropriate amounts, the waters of hydration are retained to drive the reaction to substantial completion. Additionally, calcium sulfate is formed leaving no interfering complex ions in the final product.

Chelation can be confirmed and differentiated from mixtures of components by infrared spectrometer analysis (hereinafter "IR"). Essentially, bond stretching and absorption caused by bond formation are analyzed by peak comparison. By utilizing IR, the complexes described in the Rummel patents show a substantial amount of free, unreacted glycine. However, the IR scans also indicate that some chelates and complexes are formed.

As applied in the field of mineral nutrition, there are a few allegedly "chelated" products which are commercially utilized. The first is referred to as a "metal proteinate." The American Association of Feed Control officials (AAFCO) has defined a "metal proteinate" as the product resulting from the chelation of a soluble salt with amino acids and/or partially hydrolyzed proteins. Such products are referred to as the specific metal proteinate, e.g., copper proteinate, zinc proteinate, etc. This definition does not contain any requirements to assure that chelation is actually present. On the basis of the chemical reactant possibilities, there are some real reservations as to the probability of chelation occurring to any great degree. For example, the inclusion of partially hydrolyzed proteins as suitable ligands and the term "and/or" in reference to such ligands implies that products made solely from partially hydrolyzed protein and soluble salts would have the same biochemical and physiological properties as products made from combining amino acids and soluble metal salts. Such an assertion is chemically incorrect. Partially hydrolyzed protein ligands may have molecular weights in the range of thousands of daltons and any bonding between such ligands and a metal ion may be nothing more than a complex or some form of ionic attraction, i.e., the metal drawn in close proximity to carboxyl moiety of such a ligand.

While some products marketed as metal proteinates during the 1960's and 1970's were true chelates, this was prior to the adoption of the AAFCO definition. An analysis of products currently marketed as metal proteinates reveals that most, if not all, are mixtures of metal salts and hydrolyzed protein or complexes between metal salts and hydrolyzed protein. Most are impure products which are difficult to analyze and are not consistent in protein make-up and/or mineral content.

The second product, referred to as an "amino acid chelate," when properly formed, is a stable product having one or more five-membered rings formed by reaction between the carboxyl oxygen, and the α-amino group of an α-amino acid with the metal ion. Such a five-membered ring is defined by the metal atom, the carboxyl oxygen, the carbonyl carbon, the α-carbon and the α-amino nitrogen. The actual structure will depend upon the ligand to metal mole ratio. The ligand to metal mole ratio is at least 1:1 and is preferably 2:1 but, in certain instances, may be 3:1 or even 4:1. Most typically, an amino acid chelate may be represented at a ligand to metal ratio of 2:1 according to Formula 1 as follows:

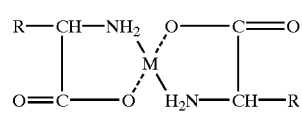

Formula 1

In the above formula, the dashed lines represent coordinate covalent bonds, covalent bonds, or ionic bonds. The solid lines between the α-amino group and the metal (M) are covalent or coordinate covalent bonds. When R is H, the amino acid is glycine which is the simplest of the α-amino acids. However, R could be a radical forming any other of the other twenty or so naturally occurring amino acids derived from proteins. These all have the same configuration for the positioning of the carboxyl oxygen and the α-amino nitrogen. In other words, the chelate ring is defined by the same atoms in each instance.

The American Association of Feed Control Officials (AAFCO) have also issued a definition for an amino acid chelate. It is officially defined as the product resulting from the reaction of a metal ion from a soluble metal salt with amino acids with a mole ratio of one mole of metal to one to three (preferably two) moles of amino acids to form coordinate covalent bonds. The average weight of the hydrolyzed amino acids must be approximately 150 and the resulting molecular weight of the chelate must not exceed 800. The products are identified by the specific metal forming the chelate, e.g., iron amino acid chelate, copper amino acid chelate, etc.

The reason a metal atom can accept bonds over and above the oxidation state of the metal is due to the nature of chelation. In one embodiment of Formula 1, it is noted that one bond is formed from the carboxyl oxygen and the other bond is formed by the α-amino nitrogen which contributes both of the electrons used in the bonding. These electrons fill available spaces in the d-orbitals. This type of bond is known as a dative bond or a coordinate covalent bond and is common in chelation. Thus, a metal ion with a normal valency of +2 can be bonded by four bonds when fully chelated. When chelated in the manner described the divalent metal ion, the chelate is completely satisfied by the bonding electrons and the charge on the metal atom (as well as on the overall molecule) is zero. This neutrality contributes to the bioavailability of metal amino acid chelates.

The structure, chemistry and bioavailability of amino acid chelates is well documented in the literature, e.g. Ashmead et al., Chelated Mineral Nutrition, (1982), Chas. C. Thomas Publishers, Springfield, Ill.; Ashmead et al., Intestinal Absorption of Metal Ions, (1985), Chas. C. Thomas Publishers, Springfield, Ill.; Ashmead et al., Foliar Feeding of Plants with Amino Acid Chelates, (1986), Noyes Publications, Park Ridge, N.J.; U.S. Pat. Nos. 4,020,158; 4,167,564; 4,216,143; 4,216,144; 4,599,152; 4,774,089; 4,830,716; 4,863,898; and 4,725,427, the entire teachings of which are incorporated by reference.

Amino acid chelates can also be formed using small peptide ligands instead of single amino acids. These will usually be in the form of dipeptides, tripeptides and sometimes tetrapeptides because larger ligands have a molecular weight which is too great for direct assimilation of the chelate formed. Generally, peptide ligands will be derived by the hydrolysis of protein. However, peptides prepared by conventional synthetic techniques or genetic engineering can also be used. When a ligand is a di- or tripeptide, a radical of the formula $[C(O)CHRNH]_eH$ will replace one of the hydrogens attached to the nitrogen atom in Formula 1. R, as defined in Formula 1, can be H, or the residue of any other naturally occurring amino acid and e can be an integer of 1, 2 or 3. When e is 1 the ligand will be a dipeptide, when e is 2 the ligand will be a tripeptide and so forth.

Based upon what is known about the production of amino acid chelates, it would be useful to provide compositions and methods of preparing amino acid chelates and complexes by improving upon the processes disclosed in U.S. Pat. Nos. 2,877,253 and 2,957,806. Specifically, by preparing chelates and complexes under dry conditions and in an enclosed environment, amino acid chelates may be prepared in a manner that is simple wherein the product produced is stable, granular, dense, dry, and free flowing.

SUMMARY OF THE INVENTION

Compositions and methods are disclosed wherein particulate amino acids are blended with particulate hydrated metal sulfate salts. The blend is then placed in an enclosed (preferably virtually sealed) environment and heated under low to moderate temperatures for a time sufficient that the waters of hydration from the hydrated metal sulfate salt are released and provide the moisture necessary to effect a bonding reaction between the electron rich functional groups of the amino acid ligand with the metal ion of the sulfate salt, thereby forming amino acid chelates and complexes.

DETAILED DESCRIPTION OF THE INVENTION

Before the present invention is disclosed and described, it is to be understood that this invention is not limited to the particular process steps and materials disclosed herein because such process steps and materials may vary somewhat. It is also to be understood that the terminology used herein is used for the purpose of describing particular embodiments only. The terms are not intended to be limiting because the scope of the present invention is intended to be limited only by the appended claims and equivalents thereof.

It must also be noted that, as used in this specification and the appended claims, the singular forms "a," "an," and "the" include plural referents unless the content clearly dictates otherwise.

The terms "metal" and "mineral" may be used interchangeably.

"Hydrated metal sulfate salt," "metal sulfate hydrate," or "metal sulfate salt having waters of hydration" includes any metal sulfate salt that has one or more waters of hydration capable of being released in the reactions of the present invention.

"Hydrate" is meant to include any degree of hydration attached to the metal sulfate salts, e.g., monohydrate, dihydrate, trihydrate, tetrahydrate, pentahydrate, hexahydrate, septahydrate, octahydrate, nonahydrate, etc. Typically, from about 1 to 15 waters of hydration will be present.

"Nutritionally relevant metals" include metals that are known to be needed by living organisms, particularly plants and mammals, including humans. Metals such as calcium copper, zinc, iron, cobalt, magnesium, manganese, chromium, among others are exemplary of nutritionally relevant metals.

"Amino acid chelates and complexes" is meant to include metal ions bonded to amino acid ligands forming heterocyclic rings. The bonds may be coordinate covalent, covalent, and/or ionic at the carboxyl oxygen group. However, at the α-amino group, the bond is typically a coordinate covalent bond.

"Enclosed chamber" or "enclosed environment" shall include any system or container that is capable of being substantially sealed or closed such that the waters of hydration released from a hydrate are substantially retained, thereby providing moisture to drive any reaction within the system or container.

With this in mind, compositions and methods of preparing amino acid chelates and complexes by blending and heating an amino acid ligand with a hydrated metal sulfate salt in an enclosed environment are disclosed and described. The compositions and methods of preparing the amino acid chelates and complexes of the present invention comprise the steps of (a) combining a hydrated metal sulfate salt and an amino acid ligand to form a particulate blend, wherein the ligand to metal molar ratio is from about 1:1 to 4:1; (b) placing the particulate blend in an enclosed environment; and (c) applying heat to the particulate blend in the enclosed environment causing the waters of hydration of the metal sulfate salt to be released into the enclosed environment. This causes a reaction resulting in the formation of an amino acid chelate or complex by effecting the reaction between functional electron rich groups of the amino acid ligand and a metal ion of the metal sulfate salt. The waters of hydration serve to provide the water necessary to enable a bonding reaction to take place between the electron rich functional groups of the amino acid ligand and the metal ion of the hydrated metal sulfate salt. This process results in particulate amino acid chelates and complexes that are stable, granular, dense, dry and/or free flowing, though in some instances, the product must be further ground prior to packaging or using the chelate for its intended purpose.

Though the preferred embodiment of the invention does not include the addition of water, some additional water may be added to effectuate desired results, e.g., copper sulfate monohydrate may not have enough waters of hydration to progress a reaction to substantial completion. Therefore, water may optionally be added in very small amounts to assist specific reactions. If water is added, the water should preferably not be added such that there is a substantial excess after the reaction has progressed to substantial completion. For example, if zinc monohydrate was used as a reactant instead of zinc pentahydrate in a formulation where zinc pentahydrate would likely drive the reaction closer to completion, 4 molar equivalents of water could be added to the blend prior to enclosing the reactants to simulate the effect of adding zinc pentahydrate. In most circumstances and in accordance with this aspect of the present invention, from about 1 to 15 molar equivalents of water can be added.

The step of enclosing the particulate blend is important because the waters of hydration must not be allowed to substantially evaporate during the reaction. This is because the waters of hydration are necessary to drive the reaction between the ligand and the metal ion of the hydrated metal sulfate salt. Therefore, a virtually sealed environment is preferred, though an enclosure that prevents substantial contact between the reaction blend and the atmosphere will also provide desired results. Specifically, the enclosed chamber may be a device such as a calorimeter, a plastic lined container, a tank, a blender, a kettle, a sealed drum, or a plastic bag capable of being enclosed or sealed. However, other enclosed chambers, environments, or systems are within the scope of the invention.

Generally, time and temperature variables should be considered when determining whether the reaction has been driven to a desired product. A typical temperature range is from about 50° C. to 100° C., though temperatures outside of this range may be used. In one embodiment, the particulate blend in the enclosed chamber may be heated to from 60° C. to 80° C. for from 2 to 4 hours. After, heating the particulate blend, the resulting product should be allowed to cool to room temperature. In other embodiments, heating may be for periods of about 15 minutes at temperatures from about 75° C. to 85° C. The heating time and temperature as well as the cooling time and temperature will depend largely upon which metal salts, ligands, ratios, batch sizes, and other variables are selected. In other words, the reaction time may be very short or may require multiple days for optimal results, depending on the embodiment.

In order for the reaction to be driven forward, the hydrated metal sulfate salt must have at least one water molecule available for release to catalyze the reaction. Thus, anhydrous forms of metal sulfate salts may not be used unless they are used in conjunction with a hydrated metal sulfate salt. However, if for example, a metal sulfate monohydrate is used, the reaction will not advance as far as other, more hydrated, metal salts. Conversely, hydrated metal sulfate salts such as a metal sulfate pentahydrate or heptahydrate (or even higher) are preferred compounds because of the number of water molecules available for liberation during the reaction. For example, ferrous sulfate heptahydrate is one of many ideal salts to utilize as will be exemplified below.

Since the ligands of the present invention are generally amino acids, the naturally occurring amino acids including alanine, arginine, asparagine, aspartic acid, cysteine, cystine, glutamine, glutamic acid, glycine, histidine, hydroxyproline, isoleucine, leucine, lysine, methionine, ornithine, phenylalanine, proline, serine, threonine, tryptophan, tyrosine, valine, and combinations thereof are preferred. However, ligands including dipeptides, tripeptides, and tetrapeptides formed by any combination of the aforementioned amino acids may be used.

If the ligand and/or hydrated metal sulfate salt is in something other than powder form, e.g. larger crystals, etc., an additional step of grinding the raw materials into powder is preferred. As such, large hydrated metal sulfate salts and ligands should be ground in to a maximum particle size of 80 mesh, preferably from 20 to 80 mesh.

There are a few major advantages to producing amino acid chelates and complexes as described above. As mentioned previously, the waters of hydration are maintained within the closed system and are used to drive the reaction forward to a greater degree than the prior art has taught. However, the enclosed chamber serves a second and important function.

Granules (usually crystals) are allowed to form under these conditions. After sufficient reaction time, the particulate blend completely changes in color and texture. Hydrated granules form that are free-flowing and generally range in size from 30 to 80 mesh. Further, while cooling, the reaction continues to progress slowly until a relatively dry, but hydrated, granule product forms which is stable, dense, dry, and free flowing. In some instances, if clumping occurs, the product may be ground into an appropriate size.

Amino acid chelates and complexes of the present invention have many possible applications. First, they may be used as plant foliars and foods. Either the product could be dissolved for use on leaves, etc., or used directly as a soil treatment. Second, the product could be dry blended in combination with other metal salts and/or a variety of ligands for more unique applications. These chelates and complexes could also be used in animal feeds by methods currently known in the art. In fact, some processes may create products that could be used in food applications, in pharmaceuticals, and/or nutritional supplements for warm-blooded animals, including humans.

EXAMPLES

The following examples illustrate compositions and methods of preparing the amino acid chelates and complexes of the present invention. The following examples should not be considered as limitations of the present invention, but should merely teach how to make the best known amino acid chelates and complexes based upon current experimental data.

In the present examples, theoretical values for final weight percentage are given rather than actual values. This has been done because it is difficult to determine an actual amount of water that remains in the compounds described below. In other words, since standard moisture tests would give artificially low moisture values, theoretical values have been assigned to the compositions for clarity. Additionally, all ratios when referring to amino acid chelate products are molar ratios.

Example 1

Glycine and ferrous sulfate heptahydrate were screened through an 80 mesh screen and dry blended together for 15 minutes at a ligand to metal molar ratio of about 1:1. Next, the blend was sealed in a plastic lined barrel and placed in an oven at 70° C. for 4 to 12 hours. The barrels were then removed from the oven and allowed to remain at room temperature for 4 to 7 days. The product produced was stable, granular, dense, dry, and free flowing. The resulting ferrous complex product contained about 18% iron and 24% moisture by weight.

Example 2

Glycine and ferrous sulfate heptahydrate were screened to about 80 mesh and dry blended together at a ligand to metal molar ratio of about 2:1. Once thoroughly admixed, the blend was sealed in a plastic lined barrel and placed in an oven for 4 to 12 hours at 70° C. The barrels were then removed from the oven and allowed to cool to room temperature where they remained for 4 to 7 days. The ferrous chelate product formed contained about 14% iron and 19% moisture by weight.

Example 3

Glycine and copper sulfate pentahydrate were screened through an 80 mesh screen and ground together in a dry blend at a ligand to metal molar ratio of about 1:1. The dry blend was placed in a sealed plastic bag and was oven dried at 70° C. for about an hour. As a result, the glycine and the copper sulfate pentahydrate began to react. Once removed from the oven, the blend was allowed to cool to room temperature and the sealed plastic bag was allowed to stand for one week. At the end of a week, a dry, stable, granular, and free-flowing product ranging from 30 to 60 mesh was formed. The resulting copper complex product contained about 22% copper and 18% moisture by weight.

Example 4

About two molar parts of glycine and one molar part of copper sulfate pentahydrate were screened through an 80 mesh screen and ground together in a dry blend. The dry blend was placed in a plastic bag and substantially sealed therein. The bag containing the blend was then oven dried at 70° C. for one hour. As a result, the glycine and the copper sulfate pentahydrate began to react. Once removed from the oven, the blend was allowed to remain at room temperature for one week while remaining sealed in the bag. At the end of the week, a dry, stable, granular, and free-flowing product ranging from 30 to 60 mesh was formed. The resulting copper chelate complex product contained about 17% copper and 15% moisture by weight.

Example 5

Glycine and manganese sulfate pentahydrate were screened through an 80 mesh screen and dry blended for 15 minutes at a ligand to metal molar ratio of about 1:1. The dry blend was sealed in a plastic bag and oven dried at 70° C. for 4 to 12 hours. Once removed from the oven, the blend was allowed to remain in the sealed bag at room temperature for about 7 days. The product formed was granular, crystalline, and stable. A manganese complex product containing about 17% manganese and 28% moisture by weight remained.

Example 6

Glycine and manganese sulfate pentahydrate were screened through an 80 mesh screen and ground together for 15 minutes at a ligand to metal molar ratio of about 2:1. The dry blend was sealed in a plastic bag and oven dried for 4 to 12 hours at 70° C. After oven drying, the blend was allowed to cool to room temperature (while remaining in the sealed bag) where it remained for 7 days. The resulting manganese chelate complex product contained about 13% manganese and 23% moisture by weight.

Example 7

Glycine and ferrous sulfate heptahydrate were screened to 80 mesh and dry blended together for 15 minutes at a ligand to metal molar ratio of about 2:1. The dry blend was then added to a sealed bomb calorimeter. The calorimeter was then submersed in a water bath maintained at 70° C. After about 15 minutes, the contents of the calorimeter reached 70° C. and began to be exothermic. The 70° C. water from the water bath was replaced by cool tap water to maintain the reaction at a temperature range between 75° C. to 85° C. When the temperature of the calorimeter dropped below 70° C., the reaction neared completion. The calorimeter containing the reaction blend was then removed from the water and allowed to return to room temperature overnight. The calorimeter was then opened and the contents were allowed to stand overnight. The resulting ferrous chelated complex product contained about 17.5% iron and 4.9% moisture by weight.

Example 8

Two molar parts of L-lysine powder and one molar part of copper sulfate pentahydrate were screened through an 80 mesh screen and dry blended together for 15 minutes. The dry blend was then added to a sealed bomb calorimeter. The calorimeter was submersed in a water bath which was maintained at 70° C. Once the contents of the calorimeter reached 70° C., the reactants began to be exothermic. The warm water was replaced by cool tap water to maintain the reaction at a temperature range of between 75° C. to 85° C. When the temperature of the calorimeter dropped below 70° C., the calorimeter containing the reacted blend was then removed from contact with the cool water and allowed to return to room temperature. After opening the calorimeter and allowwing the contents to stand overnight, a copper chelate complex containing about 19.4% copper and 5.1% moisture by weight remained.

Example 9

One mole of zinc sulfate pentahydrate powder, one mole of manganese sulfate pentahydrate powder, and four moles of glycine were screened through an 80 mesh screen and dry blended together for 15 minutes (forming a blend having a ligand to metal molar ratio of about 2:1). The dry blend was then added to a sealed bomb calorimeter. The calorimeter was submersed in a water bath maintained at 70° C. After about 15 minutes, the contents of the calorimeter reached 70° C. and began to be exothermic. The 70° C. water in the water bath was replaced by cool tap water to maintain the reaction at a temperature range between 75°C. to 85° C. When the temperature of the calorimeter dropped below 70° C., the reaction was near completion. The calorimeter containing the reacted blend was then removed from the water, allowed to return to room temperature, opened, and allowed to stand overnight. The resulting mixed metal chelate product contained about 10.1% zinc, 8.5% manganese, and 4.8% moisture by weight.

Example 10

One mole of magnesium sulfate nonahydrate powder, one mole of glycine powder, and one mole of L-methionine powder were screened through an 80 mesh screen and ground together for about 15 minutes. This procedure formed a dry blend having a ligand to metal molar ratio of about 2:1. The blend was then added to a sealed bomb calorimeter and submersed in a water bath maintained at 70° C. After about 15 minutes, the contents of the calorimeter reached 70° C. and began to be exothermic. To maintain a temperature range within the calorimeter of between 75° C. to 85° C., the 70° C. water was replaced by cool tap water. When the temperature of the calorimeter dropped below 70° C., the reaction appeared to be near completion. The calorimeter containing the reaction blend was then removed from the cool tap water and allowed to return to room temperature. After one night at room temperature, the resulting manganese mixed ligand chelate complex product contained about 6.7% magnesium and 5.5% moisture by weight.

Example 11

One mole of zinc sulfate pentahydrate powder, one mole of manganese sulfate pentahydrate powder, one mole of copper sulfate pentahydrate powder, two moles of glycine powder, two moles of L-lysine powder, and two moles of L-histidine powder were screened to 80 mesh dry blended together for 15 minutes. Thus, the blend contained a ligand to metal molar ratio of about 2:1. The blend was then placed in a sealed bomb calorimeter which was submersed in a warm water bath of about 70° C. Once the contents of the calorimeter reached 70° C., the product began to be exothermic. The warm water was replaced by cool water to maintain the reaction at a temperature range of between 75° C. to 85° C. After a while, the temperature of the calorimeter dropped below 70° C. indicating that the reaction was near completion. The calorimeter was then removed from the water and allowed to return to room temperature, opened, and allowed to stand overnight. The resulting mixed metal mixed ligand chelate complex product contained about 4.7% zinc, 3.9% manganese, 4.5% copper, and 5.0% moisture by weight.

Example 12

Glycine and ferric sulfate hydrate were screened through an 80 mesh screen and dry blended together for 15 minutes at a ligand to metal molar ratio of about 3:1. Next, the blend was sealed in a plastic lined barrel and placed in an oven at 70° C. for 4 to 12 hours. The barrels were then removed from the oven and allowed to remain at room temperature for 4 to 7 days. The ferric chelate complex product produced was stable, granular, dense, dry, and free flowing. The resulting product contained about 12% iron and 9% moisture by weight.

Example 13

Glycine and chromium potassium sulfate dodecahydrate were screened through an 80 mesh screen and ground together in a dry blend at a ligand to metal molar ratio of about 3:1. The dry blend was placed in a sealed plastic bag and was oven dried at 10 70° C. for one hour. As a result, the glycine and the copper sulfate pentahydrate began to react. Once removed from the oven, the blend was allowed to remain at room temperature for one week while remaining sealed in the bag. The resulting chromium chelate complex product contained about 8% chromium, 6% potassium, and 26% moisture by weight.

While the invention has been described with reference to certain preferred embodiments, those skilled in the art will appreciate that various modifications, changes, omissions, and substitutions can be made without departing from the spirit of the invention. It is intended, therefore, that the invention be limited only by the scope of the following claims.

We claim:

1. A method of preparing amino acid chelates and complexes comprising the steps of:
   a) combining as a particulate blend
      i) a hydrated metal sulfate salt having one or more waters of hydration, and
      ii) an amino acid ligand
   wherein the ligand to metal molar ratio is from about 1:1 to 4:1;
   b) placing said particulate blend in an enclosed environment; and
   c) applying heat to the particulate blend in the enclosed environment causing the waters of hydration of the metal sulfate salt to be released into the enclosed environment causing a reaction resulting in the formation of an amino acid chelate or complex by effecting the reaction between functional electron rich groups of the amino acid ligand and a metal ion of the metal sulfate salt.

2. A method according to claim 1 wherein said amino acid ligand is selected from the group consisting of alanine, arginine, asparagine, aspartic acid, cysteine, cystine, glutamine, glutamic acid, glycine, histidine, hydroxyproline, isoleucine, leucine, lysine, methionine, ornithine, phenylalanine, proline, serine, threonine, tryptophan, tyrosine, valine, and combinations thereof, and dipeptides, tripeptides, and tetrapeptides formed by any combination of said amino acids thereof.

3. A method according to claim 1 wherein said metal sulfate salt is selected from the group consisting of iron sulfate hydrates, copper sulfate hydrates, zinc sulfate hydrates, manganese sulfate hydrates, cobalt sulfate hydrates, magnesium sulfate hydrates, chromium sulfate hydrates, and combinations thereof.

4. A method according to claim 1 wherein the particulate blend in the enclosed environment is heated at temperatures from 50° C. to 100° C.

5. A method according to claim 1 wherein following the heating step, the temperature of the particulate blend is reduced to room temperature and allowed to continue to react.

6. A method according to claim 2 wherein the amino acid ligand is glycine.

7. A method according to claim 2 wherein the amino acid ligand is comprised of glycine and one of the other naturally occurring amino acids.

8. A method according to claim 3 wherein the hydrated metal sulfate salt is selected from the group consisting of ferrous sulfate tetrahydrate, ferrous sulfate heptahydrate, ferric sulfate hydrate, copper sulfate pentahydrate, manganese sulfate pentahydrate, zinc sulfate pentahydrate, magnesium sulfate nonahydrate, chromium sulfate heptahydrate, chromium potassium sulfate dodecahydrate, and combinations thereof.

9. A method according to claim 1 having a preliminary step of grinding said ligand and said hydrated metal sulfate salt into powder from about 20 to 80 mesh.

10. A method according to claim 1 wherein a minor amount of water is added to the particulate blend to drive the reaction toward completion.

* * * * *